US009895104B2

(12) United States Patent
Connor et al.

(10) Patent No.: US 9,895,104 B2
(45) Date of Patent: Feb. 20, 2018

(54) METHOD AND DEVICE FOR REFERENCE POINT INDENTATION WITHOUT A REFERENCE PROBE

(75) Inventors: Randall Connor, Santa Barbara, CA (US); Daniel Bridges, Goleta, CA (US); Paul Hansma, Goleta, CA (US)

(73) Assignee: The Regents of the University of California, Oakland, CA (US)

(*) Notice: Subject to any disclaimer, the term of this patent is extended or adjusted under 35 U.S.C. 154(b) by 1220 days.

(21) Appl. No.: 13/261,567

(22) PCT Filed: Jul. 12, 2011

(86) PCT No.: PCT/US2011/043768
§ 371 (c)(1),
(2), (4) Date: Jan. 16, 2013

(87) PCT Pub. No.: WO2012/015592
PCT Pub. Date: Feb. 2, 2012

(65) Prior Publication Data
US 2013/0122466 A1 May 16, 2013

Related U.S. Application Data

(60) Provisional application No. 61/368,530, filed on Jul. 28, 2010.

(51) Int. Cl.
*A61B 19/00* (2006.01)
*A61B 5/00* (2006.01)
(Continued)

(52) U.S. Cl.
CPC .......... *A61B 5/4504* (2013.01); *A61B 5/0053* (2013.01); *G01N 3/42* (2013.01); *A61C 19/04* (2013.01)

(58) Field of Classification Search
CPC ...... A61B 5/4504; A61B 5/0053; A61C 19/04
(Continued)

(56) References Cited

U.S. PATENT DOCUMENTS 5,144,753 A * 9/1992 Murphy ............... A61C 19/043
33/514
5,518,008 A * 5/1996 Cucchiaro ............ A61B 5/1111
600/590

(Continued)

*Primary Examiner* — Max Hindenburg
*Assistant Examiner* — Jonathan M Foreman
(74) *Attorney, Agent, or Firm* — Jeffrey A. McKinney; McKinney Law Group APC (57) ABSTRACT

The device performs reference point indentation without a reference probe. The indentation distance is measured relative to the instrument which remains substantially stationary during the impact process, which occurs on the order of one millisecond. In one embodiment, an impact motion with a peak force of order 28N creates an indentation in bone with a depth of approximately 150 μm during which the instrument case moves less than 1 μm. Thus the error in measuring indentation depth due to the motion of the case is less than 1%, making a reference probe unnecessary. Further, this "error" is consistent and can be corrected. In one embodiment, the device measures the fracture resistance of hard tissues by actually creating microscopic fractures in the hard tissues in a measured way. It creates these microscopic fractures by impacting the sample with a sharpened probe. The indentation distance in the sample is correlated with fracture resistance.

19 Claims, 11 Drawing Sheets (51) Int. Cl.
*G01N 3/42* (2006.01)
*A61C 19/04* (2006.01)

(58) Field of Classification Search
USPC .................................. 600/552, 553
See application file for complete search history.

(56) References Cited

U.S. PATENT DOCUMENTS

| | | | |
|---|---|---|---|
| 6,068,604 A | 5/2000 | Krause et al. | |
| 2003/0233112 A1* | 12/2003 | Alden | A61B 5/1405 606/181 |
| 2004/0147932 A1 | 7/2004 | Burkinshaw et al. | |
| 2007/0276292 A1 | 11/2007 | Hansma et al. | |
| 2009/0093692 A1 | 4/2009 | Hansma | |
| 2011/0311944 A1* | 12/2011 | Earthman | A61B 9/00 433/119 |

* cited by examiner

Fig. 12C

METHOD AND DEVICE FOR REFERENCE POINT INDENTATION WITHOUT A REFERENCE PROBE

RELATED APPLICATION

This Application is a national phase application being filed under 37 CFR 371 based on International application No. PCT/US2011/043768 having an International filing date of Jul. 12, 2011, which claims priority to U.S. Provisional Patent Application No. 61/368,530 filed on Jul. 28, 2010. Priority to the provisional patent application is claimed pursuant to 35 U.S.C. §§119. The above-noted patent applications are incorporated by reference as if set forth fully herein.

STATEMENT REGARDING FEDERALLY SPONSORED RESEARCH OR DEVELOPMENT

This invention was made with Government support under Grant No. ROI GM 065354, awarded by the National Institutes of Health. The Government has certain rights to this invention.

FIELD OF THE INVENTION

The field of the invention generally relates to devices and methods for indentation without a reference probe, for measuring hardness and/or fracture resistance of materials.

BACKGROUND OF THE INVENTION

Various devices have been proposed to measure properties of tissues. For instance, U.S. Pat. No. 6,068,604 discloses a cartilage indentor instrument for measuring the compressive properties of cartilage. Other devices exist for harder tissue such as bone. For example, the Osteopenetrometer was designed for in vivo testing of trabecular bone during surgical procedures. That instrument was developed to characterize the mechanical properties of trabecular bone to obtain information relevant to reducing the problem of implant loosening following total knee arthroplasty. The Osteopenetrometer involved penetrations of lengths of over 8 millimeters and widths of over millimeters in diameter at implant sites during surgery.

More recently, devices have been proposed that utilize both a test probe and in most cases a reference probe for use in testing hard material such as bone tissue. Movement of the test probe relative to a reference probe is used to determine one or more parameters of the material being tested. Examples of these devices may be found, for instance, in U.S. Publication Patent Application No. 2007-0276292 and 2009-0093692 by common inventors of this application, and these applications are incorporated by reference. Devices such as those illustrated in the '292 and '692 Applications that use reference probes for some applications require a user to scrape away the periosteum, a technique requiring training, for in vivo use with a reference probe. Significant discussion of hardness and fracture measurements made with such instruments is found in the incorporated references.

SUMMARY

In one aspect of the invention the device performs reference point indentation on a wide variety of materials without a reference probe. The indentation distance is measured relative to the case of the instrument which remains substantially stationary during the impact process, which occurs in times of order one millisecond. Specifically, for a specific embodiment an impact with a peak force of order 28N creates an indentation in bone with a depth of approximately 150 µm during which the case of the instrument moves less than 1 µm. Thus the error in measuring indentation depth due to the motion of the case is less than 1%, making a reference probe unnecessary. Further, this "error" is consistent and can be corrected for if necessary. In a specific embodiment, the device measures the fracture resistance of hard tissues by actually creating microscopic fractures in the hard tissues in a measured way. It creates these microscopic fractures by impacting the sample with a sharpened probe. The indentation distance in the sample is correlated with fracture resistance.

In one embodiment, a probe device for indentation of a material without the use of a reference probe includes a housing having a mass and a force generator configured to apply a predetermined force for a predetermined period of time. The probe device includes a test probe having a proximal end operatively coupled to the force generator. The device further includes a force generator trigger and a measurement device configured to monitor the displacement of the test probe upon actuation of the trigger wherein the housing mass, the predetermined force applied by the force generator, and the predetermined time the force is applied are selected such that the housing remains substantially stationary during displacement of the test probe.

In another embodiment, a method of indenting a material includes placing a probe device having a test probe adjacent the material, the probe device having a housing having a suitable mass, a force generator operatively coupled to the test probe, the probe device further having a measurement device configured to monitor the displacement of the test probe. The force generator is triggered to apply a predetermined force over a predetermined time to the test probe. The material is indented wherein the force and time of the force applied to the probe are such that the housing remain substantially stationary during displacement of the test probe. The method further includes measuring the displacement of the test probe.

DETAILED DESCRIPTION OF THE ILLUSTRATED EMBODIMENTS

Figure 1:
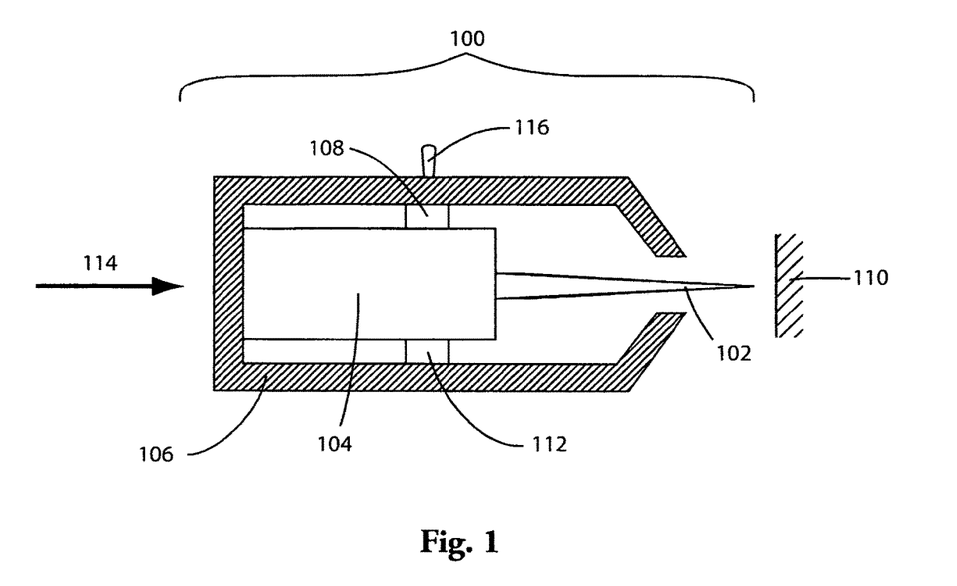
FIG. 1 illustrates a schematic illustration of a probe device according to one embodiment.

For indentation measurements on materials with an overcoating of softer substances, such as bone surrounded by soft tissue, it is generally necessary to use what the inventors refer to as "Reference Point Indentation". That is, the indentation distance cannot be measured absolutely relative to some rigid frame because the soft material will deform an unknown amount under the probe. In prior disclosures by the inventors, a reference probe is typically employed, such as a specially sharpened hypodermic needle for bone measurements. This reference probe sits on the surface of a sample to establish the reference point. Indentation distances for a separate test probe are measured relative to this reference point FIG. 1 shows a generalized schematic view of the probe device 100 according to one embodiment. A probe 102 is connected to a force generator 104 held in a case or outer housing 106. A trigger 108 initiates the force generator 104 to impart a predetermined force acting over a time of preferably about 1 millisecond or less to accelerate the probe 102 along its long axis into a sample 110, producing an indentation event. A measurement device 112 monitors the displacement of the probe 102 into the sample 110 during the indentation event produced by the force generator 104. The trigger 108 triggers the event when the force 114 applied to the outer housing 106 reaches a threshold value or when an optional trigger switch 116 is activated. In the case of a soft material covering a harder material such as skin over bone, the probe device 100 is designed such that the trigger force is more than required to penetrate the soft layer and establish an initial indention in the material of interest. For skin over bone, a probe of hypodermic dimensions is suitable.

The probe device 100 eliminates the need for a reference probe. Referring to FIG. 1, the reference point is the point that the probe 102 reaches in the sample just before an indentation event is triggered. The indentation distance increase from this reference point that results from the indentation event is measured with measurement device 112. This is possible because the mass of the instrument body 106, the force and the force application time are chosen such that the inertia of the body of the instrument 106 keeps it substantially fixed in space during the short time of the event. Thus, the distance measured with measurement device 112 is the same as the distance that the probe 102 further indents the sample from the reference point. By way of example, a time on the order of 1 millisecond for a force of 10-20 newtons with a handheld sized body and a hypodermic sized probe would result in such inertial constraint such that the error caused by the movement of the instrument body 106 would be less than one percent. The elimination of the reference probe has the advantage of simplicity and of eliminating the possibility of soft tissue buildup and friction between the test probe and the reference probe when the instrument is used to penetrate soft tissue covering bone. Although the preferred embodiment for such an instrument is a handheld measurement device, the principle leading to making measurements without a reference probe apply equally well to other instrument geometries.

Figure 2A:
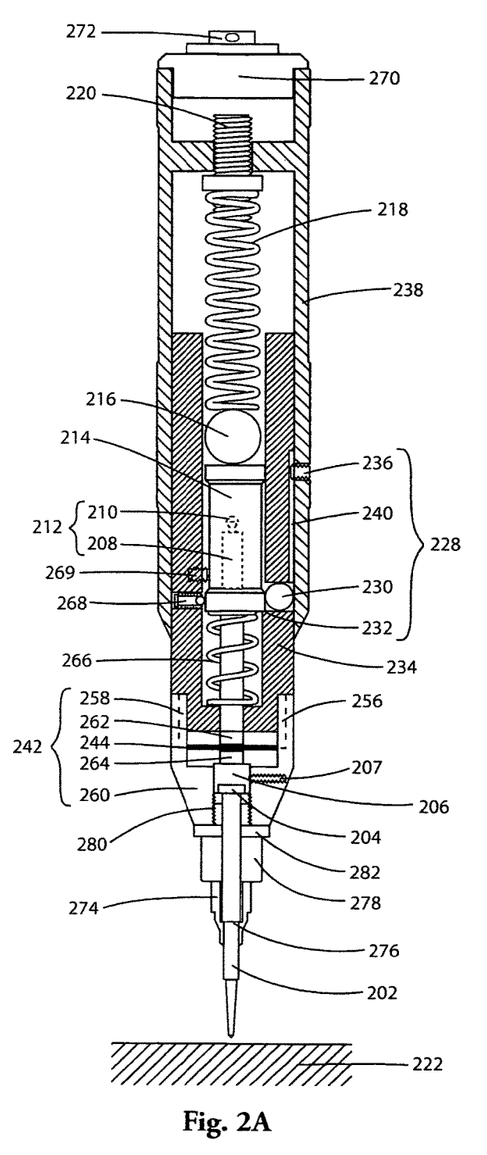
FIG. 2A illustrates a side, cross-sectional view of a device according to a particular spring biased/impact mass embodiment of the invention.
Figure 8:
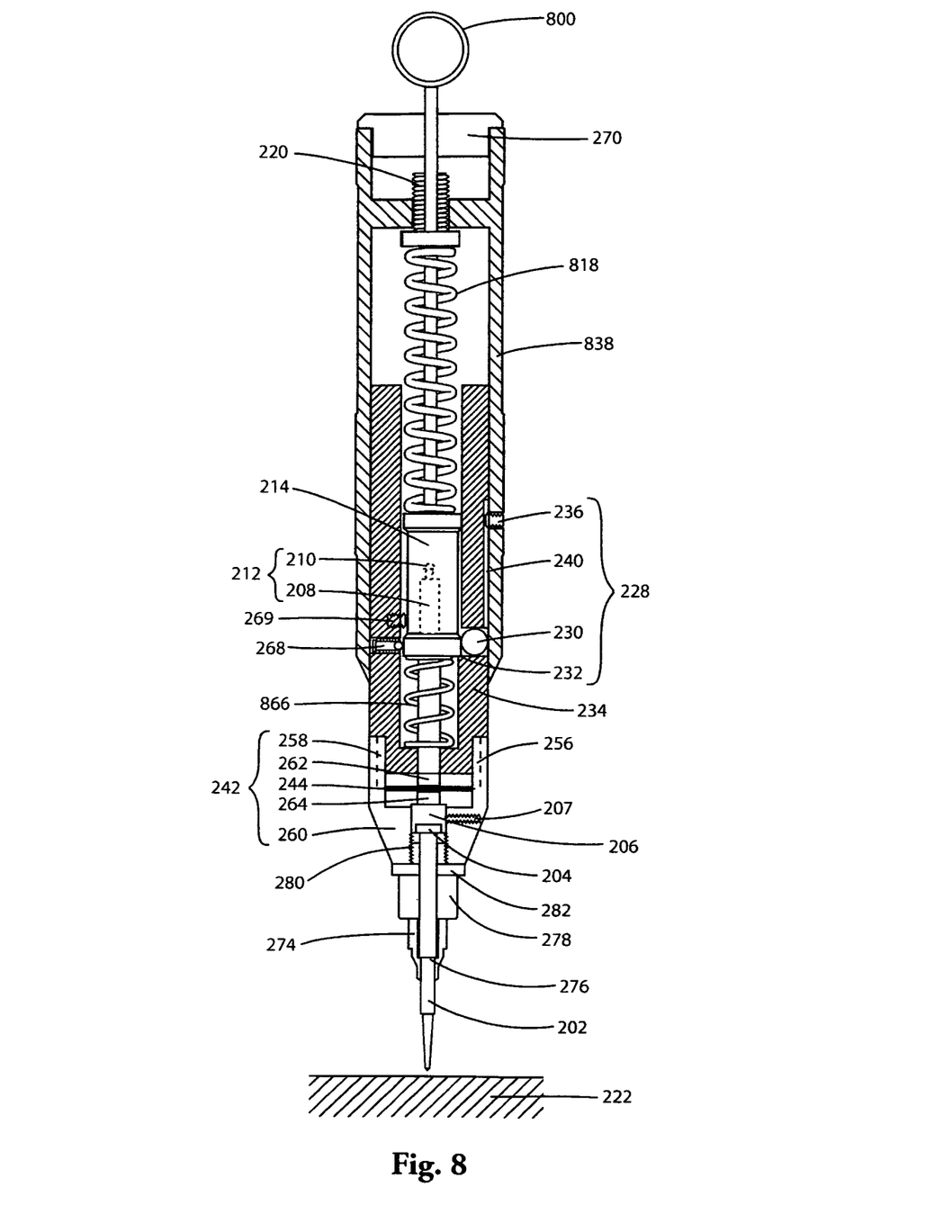
FIG. 8 is still another embodiment of a probe device.

One skilled in the art will recognize that a variety of possible implementations could be employed for the elements in FIG. 1. Force generator 104 and trigger 108 may be electronic in nature or mechanical. As examples: (1) the force generator 104 and trigger 108 could consist of a mass on a spring that was compressed in preparation for a test and then released with the trigger 108 to impact the test probe 102 to perform the test, as shown in FIGS. 2 and 8; (2) the force generator 104 and trigger 108 could consist of a solenoid that was triggered electronically such that the core of the solenoid impacted the test probe 102 to perform the test; (3) The force generator 104 and trigger 108 could consist of piezoelectric crystal that was triggered by a voltage pulse; (4) The force generator 104 and trigger 108 could consist of a voice coil actuator that was triggered by a voltage pulse; (5) The force generator 104 and trigger 108 could consist of a piston driven by a pulse of compressed gas or hydraulic fluid. A particular mechanical embodiment of the first type is described below which has advantages of simplicity, ruggedness and low cost.

FIG. 2A shows a mechanical embodiment of the invention. A test probe 202 is connected to a force generator which is in the form of an impact generator consisting of an optional magnet 204 in a probe holder 206 connected to an impact transfer rod 208 that is terminated by an impact transfer rod adjustment screw 210, which effectively changes the length of the impact transfer assembly 212 consisting of the impact transfer rod 208 and the impact transfer rod adjustment screw 210. This impact transfer rod adjustment screw 210 is impacted by an impact mass 214 that is driven by a force normalizing ball 216 driven by a primary spring 218. The impact mass is retained by set screw 269, this prevents the mass from moving upwards when the primary spring 218 is not compressed. The primary spring adjustment screw 220, together with the impact transfer rod adjustment screw 210, adjusts the maximum force applied to the sample 222 during the impact.

The impact is triggered by a trigger device 228 consisting of a trigger ball 230 that pushes the impact mass 214 off a ledge 232 machined into an inner housing 234. The impact mass 214 then impacts the impact transfer assembly 212. The trigger ball 230 itself is pushed by a set screw 236 held in the outer housing 238. The set screw 236 travels down a groove 240 in the inner housing 234 as the primary spring 218 is compressed by the operator (not shown) applying a force to the outer housing 238. In this regard, the outer housing 238 moves relative to the inner housing 234 thereby building potential energy in the primary spring 218. Upon actuation of the trigger device 228, the potential energy of the primary spring 218 is then transferred into kinetic energy whereby the normalizing ball 216 contacts the impact mass 214 which, in turn, contacts the transfer rod adjustment screw 210.

A measurement device 242 monitors the displacement of the test probe 202 in the sample 220 resulting from an impact. The measurement device 242 can have several embodiments implemented to quantify the indentation measurement. As examples: (1) the measurement device 242 can measure the relative displacement of the test probe 102 with a capacitive sensor, linear variable differential transformer (LVDT), or other electronic displacement sensor; (2) the measurement device 242 can measure the relative displacement of the test probe with a mechanical mechanism such as used in machinist's dial gauges. The measurement device in one embodiment 242 consists of a flexure assembly 244 consisting of a flexure 246 made of Beryllium Copper with strain gauges 248, 250, 252, 254 as shown in detail FIG. 2B. The ends of the flexure assembly 244 rest in grooves 256 and 258 in the nose cone 260. The center of the flexure assembly has a hole that slips over the impact transfer rod 208 and is held in place by an upper stop 262 and lower stop 264.

After an impact the secondary spring 266 pushes the impact mass 214 back up the inner housing 234. The impact mass is pushed laterally by a ball plunger 268 onto the ledge 232, ready for the next impact (if needed). The end cap 270 can have an optional leveling indicator 272, such as a bubble level, so the operator can monitor the orientation of the device during operation, if desired.

Figure 2B:
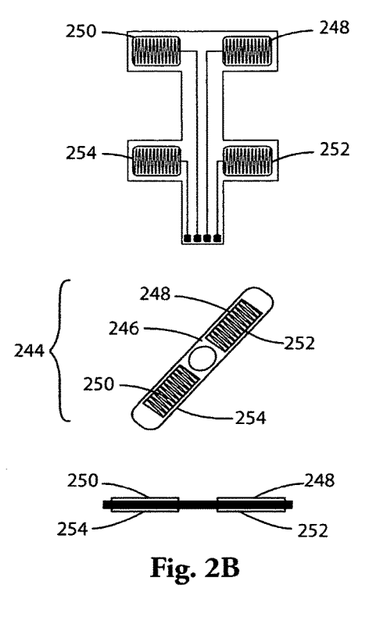
FIG. 2B illustrates side and top views of a flexure assembly.

The flexure assembly 244 requires a calibration to convert the output voltage to microns. This requires a custom setup consisting of a calibrated displacement transducer and a voice coil to provide a given displacement. The flexure assembly 244 is displaced by a ramp function generated by the calibration device with known displacements. The output voltage from the flexure assembly 244 is recorded and a linear regression models the relationship between the output voltage of the flexure assembly and the known displacements to provide an accurate calibration for the flexure assembly 244. Alternately, if measurements are reported as ratios of indentation distances into a reference material relative to indentation distances into the material under test, then the need for absolute measurements is decreased. It is still, however, useful to have a rough idea of absolute measurements to be sure that the ratios come from comparable absolute measurements in different instruments.

Figure 2C:
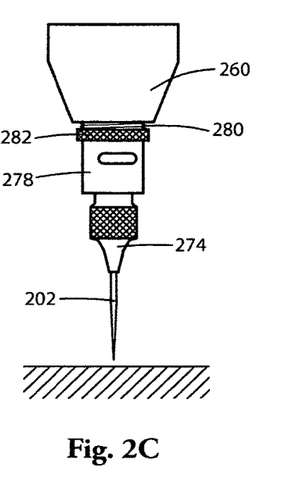
FIG. 2C illustrates a side view of the distal end of the device of the type illustrated in FIG. 1.

Referring to FIGS. 2A and 2C, an optional guide 274 is provided that guides the probe 202 during the impact. It can be sterilized together with the probe 202 as a disposable sterile assembly for use on humans or living animals. An additional advantage of using the optional guide 274 is that the probe 202 can be machined to have a probe stop 276 that retains the probe in the device as it is removed from the sample 222. The optional guide 274 is held in an optional guide holder 278 which in turn is held in the nose cone 260 by a threaded region 280 with a threaded locking nut 282. The optional guide holder 278 can for example be a Luer lock socket that holds a Luer lock hub on the guide 274.

FIGS. 3A-3D show several preferred probes 202a which can be used. The probe 202a in FIG. 3A, consists of a main body 310, a guide portion 306, a probe stop 308, a shaft 304, and a tip 302. The probe stop 308 prevents the probe from being removed during retraction by the guide 274 (FIG. 2A). The probe design in FIG. 3A allows for easy penetration without the use of any type of hypodermic needle to cut through the soft tissue such as skin. The tip 302 of the probe 202a is 90 degrees and conical with a very sharp point (less than 0.0004" radius). This sharp tip allows for the probe to pierce through the soft tissue easily. Other tips have been experimented with such as different conical tip angles varying from 10 to 120 degrees, as well as other tip geometries including cube corners, and wedges for bone. For testing other materials flat and spherical tips have been used as well.

Figure 3A:
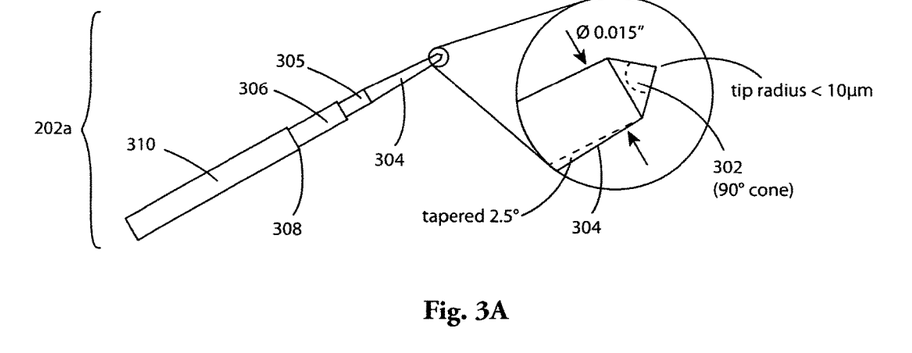
FIG. 3A illustrates a view of a test probe according to one embodiment.

The conical tip 302 has a maximum diameter (0.015"+/−0.0005") that is small enough to allow it to pierce soft tissue with a low force, but is also large enough to transfer enough force from the force generator 104 to induce micro-fractures in the sample. For the case of skin over bone, the initial force applied to the tip before the primary impact (about 11 N) is high enough to pierce through the periosteum. After the conical tip 302 there is a tapered section 304 with a taper of 2.5 degrees from normal to a total length of 0.4 in. This allows for the probe to support the high impact forces that are transferred down to the tip and into the sample. There is an additional 0.2 in. non-tapered section 305 which allows for samples or patients with thicker soft tissue to be tested without interference from the probe guide portion 306. The current embodiment is composed of 440C hardened stainless steel; however, other materials could be used for testing different samples, such as tungsten carbide for extremely hard samples. A diamond tip could be used as well.

Figure 3B:
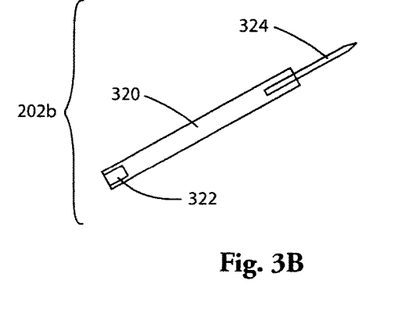
FIG. 3B illustrates a view of a test probe according to another embodiment.

FIG. 3B shows another preferred probe 202b consisting of body 320, magnet 322, and shaft 324. The probe magnet 322 allows the probe 202b to be connected to the optional magnet 204 (FIG. 2A) in the probe holder 206 (FIG. 2A). A set screw 207 can be used to clamp down the probe holder for maintenance or disassembly if desired.

Figure 3C:
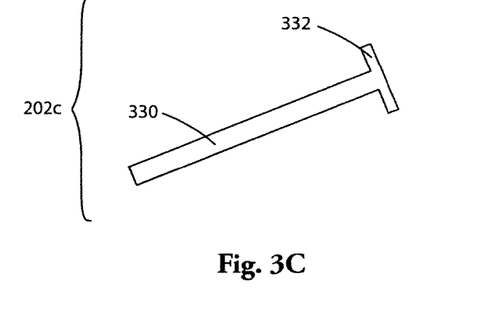
FIG. 3C illustrates a view of a test probe according to another embodiment.

FIG. 3C illustrates a probe 202c that consists of a main shaft 330 and a wider indentation face 332 which can be used to test soft tissues such as skin, cartilage, and gels. The wider indentation face helps distribute the impact force over a larger area rather than one small point, which enables the instrument to detect indentation properties of soft tissues.

Figure 3D:
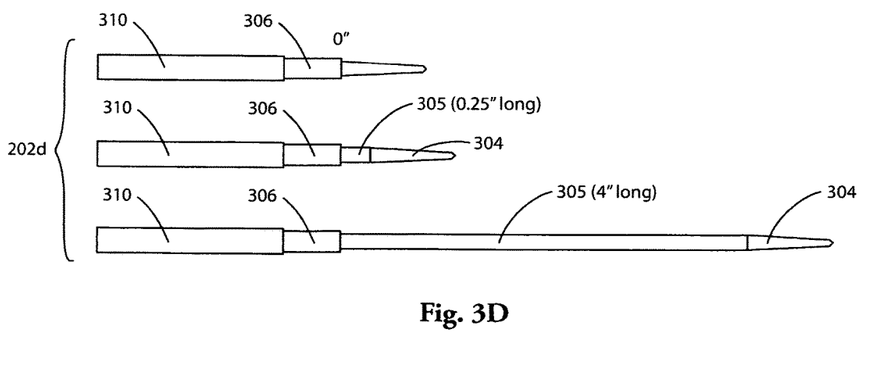
FIG. 3D illustrates a view of a test probe according to another embodiment.

FIG. 3D shows a probe 202d that is a modified version of the probe 202 illustrated in FIG. 3A that allows for testing bone that would be covered with thinner or thicker soft tissue, such as the tibia or the femur. The probes are very similar, except the non-tapered section 305 varies in length from 0" up to 4".

Figure 4A:
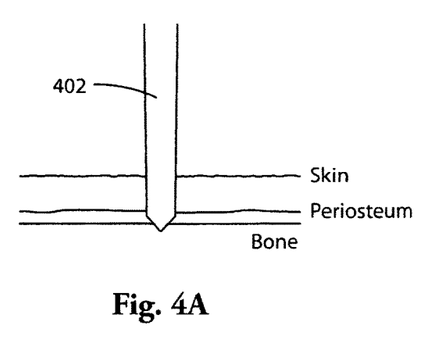
FIG. 4A illustrates one mode of operation of the device.
Figure 4B:
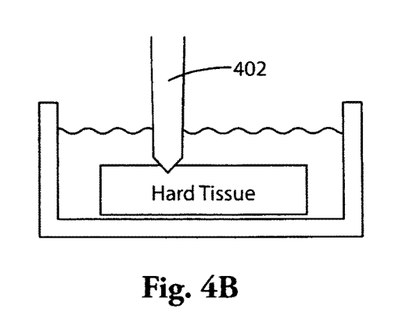
FIG. 4B illustrates another mode of operation of the device.
Figure 4C:
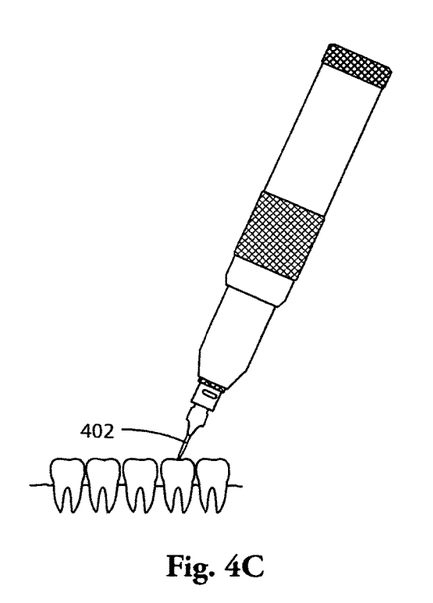
FIG. 4C illustrates still another mode of operation of the device.

FIGS. 4A-4C shows possible uses of the described invention. FIG. 4A shows a probe 402 as it would be used on a living animal or human. The probe 402 is inserted through the skin and periosteum, until the probe 402 has made an indentation into the bone. Both the conical tip 302 and part of the shaft 304 (FIG. 3A) of the probe 402 may be inserted into the bone during use. FIG. 4B demonstrates the use of the probe device 402 on a hard tissue sample such as bone, dentin, enamel or synthetic hard tissue. The hard tissue sample can be held in an optional vice or clamp and is able to be tested while submersed in fluid. Again, both the conical tip 302 and part of the shaft 304 is inserted in the sample (FIG. 3A). FIG. 4C shows the probe 402 being used in vivo on a tooth in a patient's or animal's mouth.

Figure 5A:
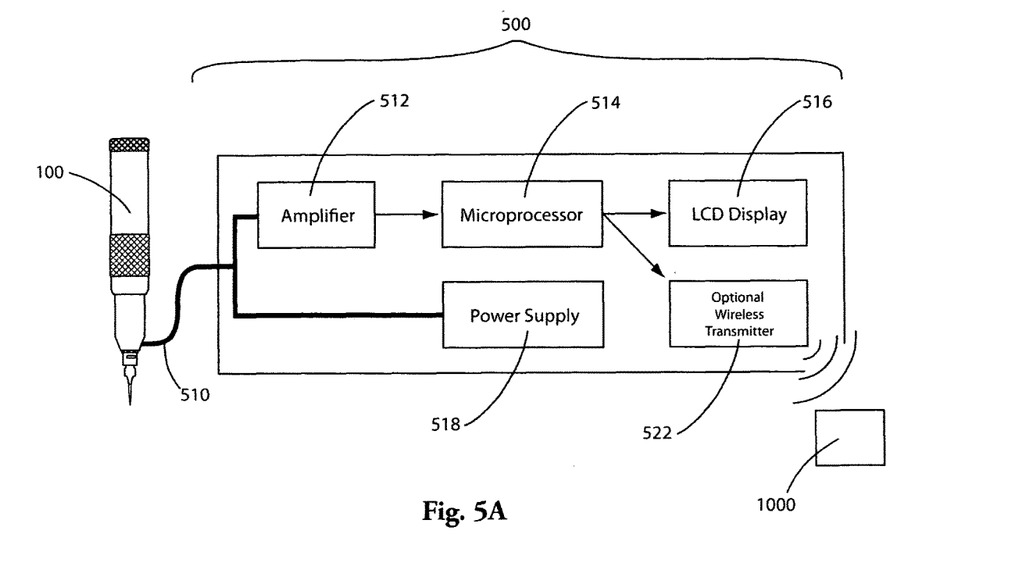
FIG. 5A illustrates a probe device along with an external electronics unit for power and data acquisition.

FIG. 5A shows one embodiment of the electronics unit 500 used to power and receive measurement signals from the main probe device 100. The electronics unit 500 has power and data acquisition functionality. A connecting cable 510 connects the flexure assembly 244 (FIG. 2B) to the electronics unit 500. The electronics unit 500 consists of a power supply 518 which provides power to the strain gages 248, 250, 252, and 254 (FIG. 2B) in the flexure assembly 244. The electronics unit 500 also houses an amplifier 512 to amplify the signal from the strain gages 248, 250, 252, and 254, as well as a microprocessor 514 to receive and process the signal, and an LCD display 516 to display the measurement to the operator. The microprocessor 514 may include an analog to digital converter (ADC) or the ADC may be separate from the processing microprocessor 514. An optional wireless transmitter 522 is also available for transfer of data to a networked central data storage area

Figure 5B:
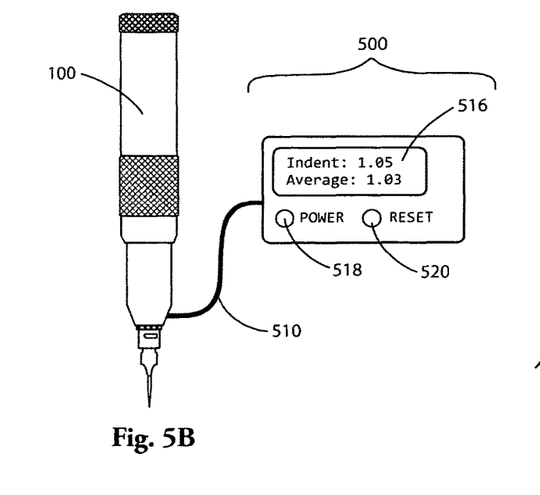
FIG. 5B illustrates a display device for displaying test results. Also included are a reset button and a power button.
Figure 5C:
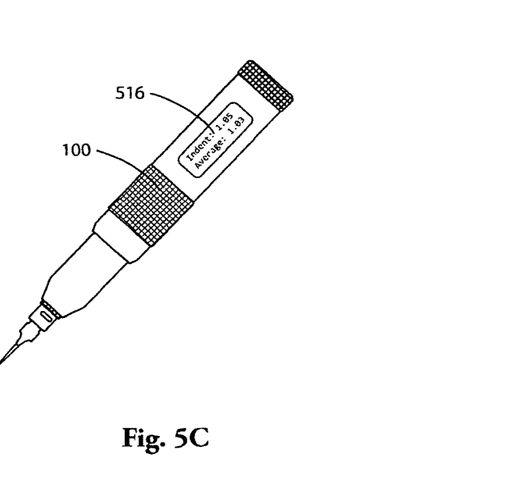
FIG. 5C illustrates a probe device with integrated power and data acquisition functionality.

1000. In one embodiment, the microprocessor 514 allows for a running average of the requested measurement mode to be displayed along with the last measurement value. Different possible measurement modes are show in FIG. 6. FIG. 5B shows the invention with attached electronics unit 500. The outside of the electronics unit 500 includes a power button 518 and a reset button 520 which allow the operator to turn the unit on and off and reset the running average. FIG. 5C shows a design where the electronics are incorporated into the probe device 100.

Figure 6:
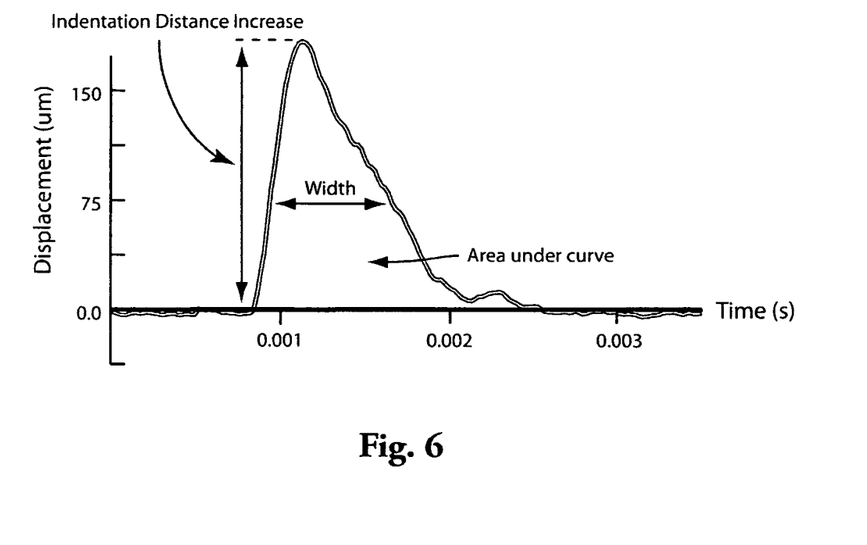
FIG. 6 is a graph illustrating displacement of the test probe as a function of time.

FIG. 6 shows a sample waveform from the strain gauges 248, 250, 252, and 254 obtained during impact. There are many different measurements which can be made using this waveform, FIG. 6 details a subset of these including impact depth, waveform width, and area under the curve. The operator will select the desired measurement mode before taking measurements. The electronics unit LCD 516 (FIG. 5) will display the most recent measurement as well as a running average of all measurements taken since the reset button 520 (FIG. 5) has been pressed or since measurements were first started.

Figure 7:
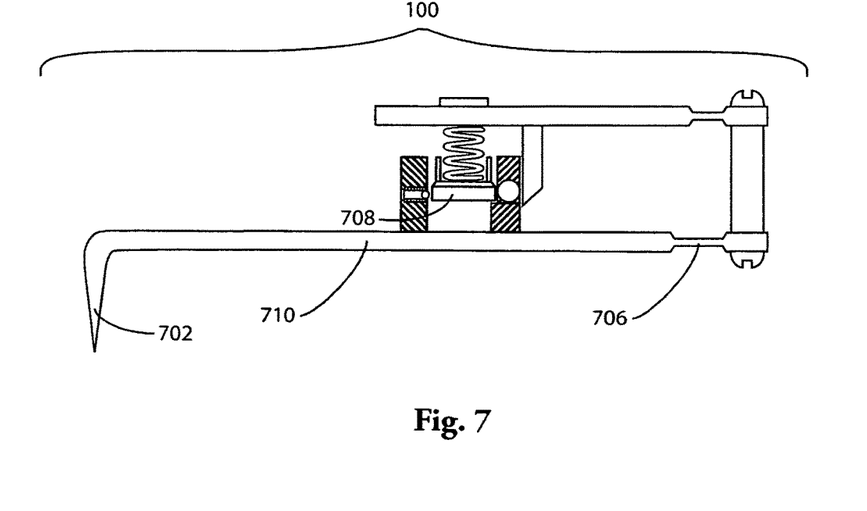
FIG. 7 is another embodiment of a probe device.

FIG. 7 shows a version of the probe device 100 intended for use in hard-to-reach positions such as dental testing or for probing bone during surgery. There are four strain gages (not shown in FIG. 7) located on flexure 706 which measure the displacement of the main beam 710 during impact from the impact mass 708. These strain gages output signals to an electronics unit much like the electronics unit 500 described with respect to FIG. 5. The internal impact and triggering mechanisms work in the same fashion as described above.

FIG. 8 illustrates a modified version of the embodiment illustrated in FIG. 2A. In this embodiment, a separate device such as a plunger 800 is used to load the primary spring 818. Instead of a force being applied to the outer housing 838 by the operator, the plunger 800 is used to apply the force to the primary spring 818 (e.g., store potential energy in the primary spring 818). The operator would push the plunger 800 inward or distally to load the primary spring 818 where the plunger 800 would lock into place. After the device triggers, either through a separate trigger button or through advancement of the outer housing 838, the plunger 800 would be turned and pulled back to the original position where it could be pushed back in for the next indentation cycle. A secondary spring 866 may assist in restoring the plunger 800 back to the starting or original position.

Figure 9:
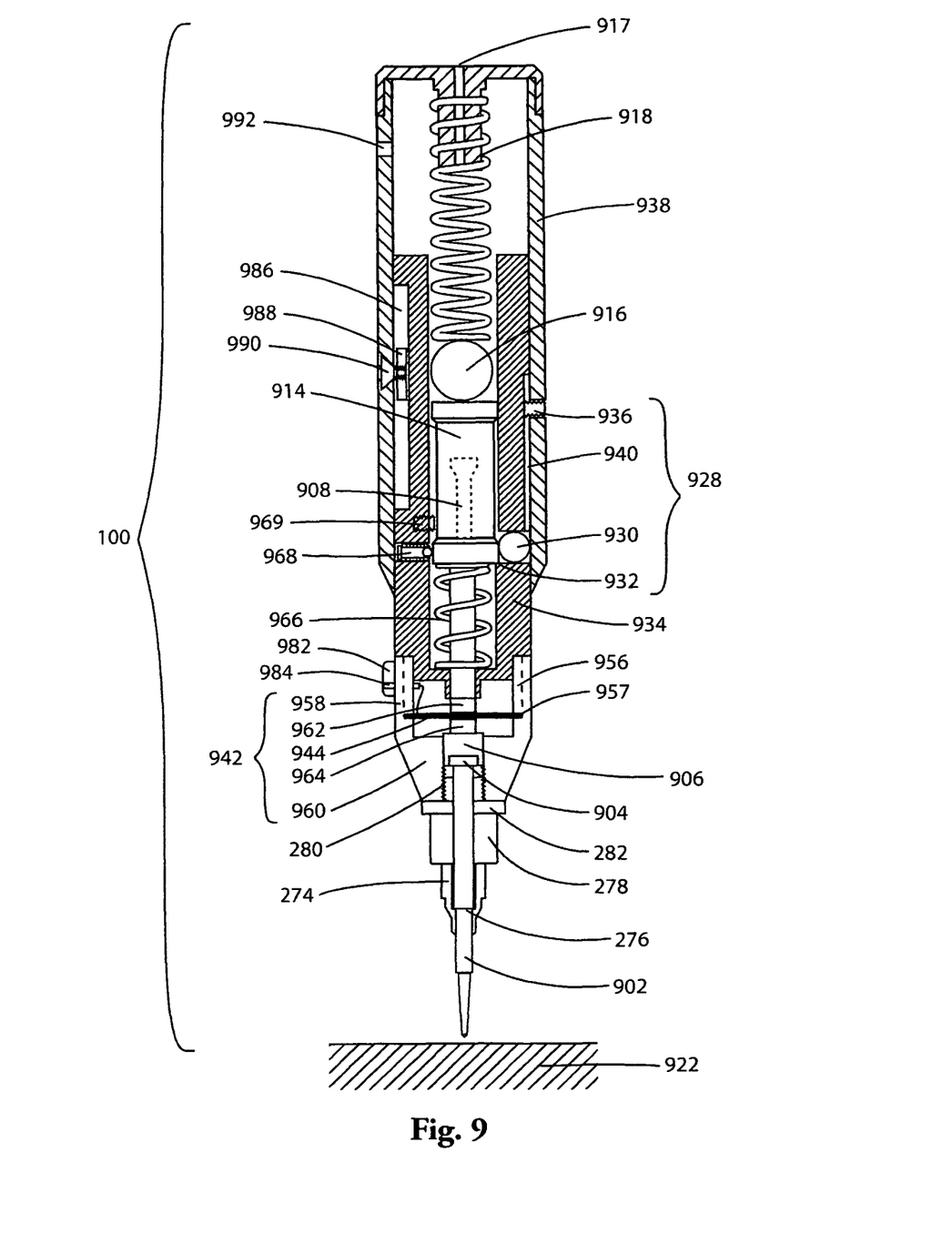
FIG. 9 illustrates yet another embodiment of the probe device.

FIG. 9 shows one preferred embodiment of the probe device 100. The total mass of this embodiment is less than 0.5 lbs making the same lightweight and easy to manipulate and use. It should be understood that the probe device 100 may weigh more or less. As seen in FIG. 9, a probe 902 is connected to an impact generator consisting of an optional magnet 904 in a probe holder 906 connected to an impact transfer rod 908. This impact transfer rod 908 is impacted by an impact mass 914 (weighing 0.011 lb) that is driven by a force normalizing ball 916 driven by a primary spring 918 with a spring constant of 1.4 lb/in. The impact mass is retained by set screw 969, this prevents the mass from moving upwards when the primary spring 918 is not compressed. The primary spring 918 is held at the other end by an end cap with a first vent hole 917, which is connected to the outer housing 938. There is a second vent hole 992 located in the side of the outer housing 938. The vent holes 917, 992 make mitigate or eliminate any contribution of trapped air to the effective spring constant of the primary spring 918.

The impact is triggered by a trigger device 928 consisting of a trigger ball 930 that pushes the impact mass 914 off a ledge 932 machined into the inner housing 934 when the primary spring is compressed to a force of 11 N. The impact mass 914 then impacts the impact transfer rod 908. The trigger ball 930 itself is pushed by a set screw 936 held in the outer housing 938. The set screw 936 travels down a groove 940 located in the inner housing 934 as the primary spring 918 is compressed by the operator (not shown) applying a force to the outer housing 938. In this regard, the outer housing 938 moves relative to the inner housing 934 thereby building potential energy in the primary spring 918. A housing alignment guide 988 is retained by a set screw 990 and follows a machined groove 986 in the inner housing 934 to maintain proper alignment when the operator compresses the outer housing 992. This allows for more precision for the trigger device 928. Upon actuation of the trigger device 928, the potential energy (e.g., around 0.17 J) of the primary spring 918 is then transferred into kinetic energy whereby the normalizing ball 916 contacts the impact mass 914 which, in turn, contacts the impact transfer rod 908.

A measurement device 942 monitors the displacement of the probe 902 in the sample 922 resulting from an impact. The measurement device 942 consists of a flexure assembly 944 consisting of a flexure 246, with a spring constant of 26.1 lb/in, made of hardened Beryllium Copper with strain gages as shown in detail in FIG. 2B. The ends of the flexure assembly 944 rest freely in grooves 956 and 958 in the nose cone 960. The center of the flexure assembly has a hole that slips over the impact transfer rod 908 and is held in place by an upper stop 962 and lower stop 964, which limits the travel of the test probe into the sample (travel limited to less than 0.014"). The reference point from which displacements are measured is the ledge 957 on the nose cone 960. The reference mass is 0.34 lb and consists primarily of the nose cone 960 and inner housing 934. Due to the short duration of the impact (less than 1 millisecond) the reference mass stays substantially fixed in time (to within approximately 1 micron), allowing for the displacement to be measured without a physical reference probe in contact with the sample.

After an impact, the secondary spring 966, with a spring constant of 1.2 lb/in, pushes the impact mass 914 back up the inner housing 934. The impact mass is pushed laterally by a ball plunger 968 onto the ledge 932 and held into place with a 0.5 lb lateral force, ready for the next impact (if needed). The end cap 917 can have an optional leveling indicator, such as a bubble level, so the operator can monitor the orientation of the device during operation, if desired.

Figure 10:
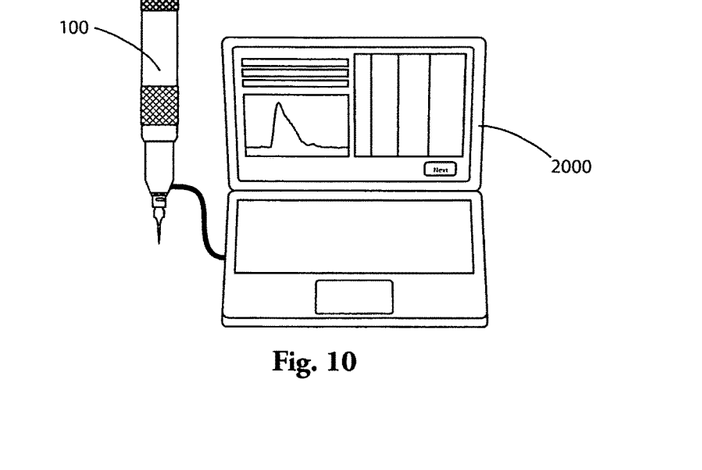
FIG. 10 illustrates the probe device interfaced to a personal computer.

In addition to handheld electronics (FIGS. 5A and 5B), more complete data can be acquired though the use of a laptop or desktop computer 2000 attached to the probe device 100 through a cable (FIG. 10). This setup could be used in an application requiring a more rigorous acquisition of data as compared to a routine diagnostic environment where the simpler handheld (FIG. 5B) or embedded (FIG. 5C) electronics would be more practical. The advanced acquisition system would record entire time-displacement curves for subsequent analysis.

Bone Material Strength (BMS) is a normalized parameter that can be calculated from the measurements acquired by the instrument. BMS is defined as 100 times the ratio of the average indentation distance increase from the impact into a calibration phantom (such as Poly(methyl-methacrylate), PMMA, plastic) divided by the indentation distance increase from the impact into the bone. Thus, if a sample was exactly as resistant to indentation as the phantom, the BMS would be 100. If the sample was more susceptible to fracturing its BMS would be lower than that of the phantom. Similarly, if the sample was less susceptible to fracturing its BMS would be higher than that of the phantom.

Figure 11A:
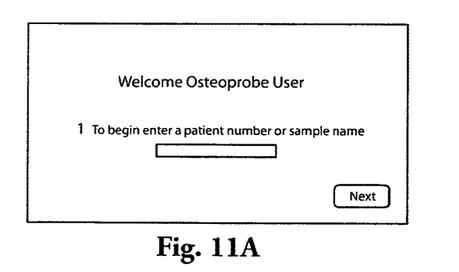
FIGS. 11A, 11B 11C, and 11D illustrate an exemplary user interface.
Figure 11B:
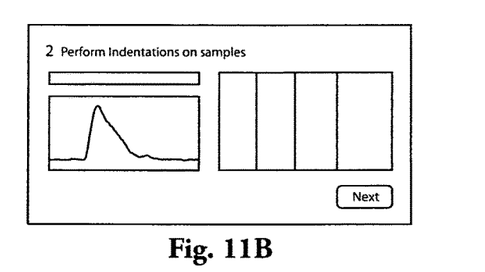

An exemplary version of computer software that may be implemented with the probe device 100 utilizes a guided acquisition process (FIG. 11A-11D). The software first begins with a welcome screen (FIG. 11A) asking the user to enter a patient name, number, experiment name, or other identifier. Once the user enters the required parameters a new experiment folder is created with the current date in the folder name. The program proceeds to the main acquisition screen (FIG. 11B). The software is now rapidly sampling the signals from the strain gauges 248, 250, 252, and 254. Any number of sampling rates may be used although sampling rates between 48 kHz and 250 kHz has been found to be sufficient.

The software includes discriminators or thresholds built therein that allow the software to search for only pertinent signals and reject spurious or false readings such as a false reading from inserting the probe. These discriminators work by looking at the rate of rise in the signal from the baseline to the peak height (FIG. 6). Because the impact is reproducible and of a consistent time scale, one can determine the useful signals by monitoring the input and looking only for signals which rise from baseline by at least 100 microns in less than 1 ms. These discriminators can be adjusted depending upon the material being sampled or the probe being used.

When the user performs an indentation of material using the probe device 100 the software automatically captures the waveform (FIG. 6) and saves a data file for each individual waveform. The software also optionally calculates useful parameters from the captured waveform like indentation distance increase, area under the curve, Bone Material Strength (BMS), and others. These parameters are compiled and saved to an additional data file.

Figure 11C:
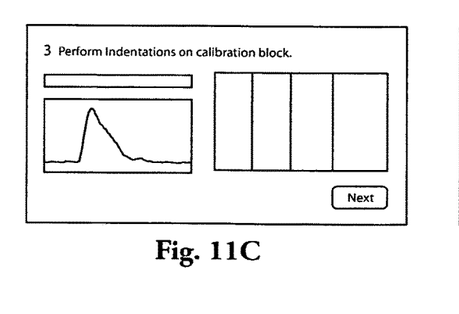
Figure 11D:
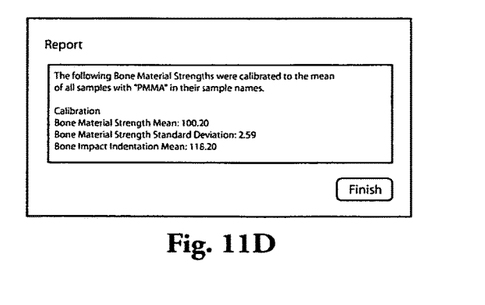

Once the user has performed all of their indentations, the process is advanced, for example, by pressing a next button or the like to proceed to the calibration screen (FIG. 11C). This screen is very similar to the main acquisition screen, but is only used to indent the calibration or phantom material, which may in the form of a calibration block. The user performs five or more indentations on the calibration block to ensure that the instrument is performing properly. These values are monitored to ensure they remain in the specifications given. One exemplary calibration material is Poly(methyl-methacrylate) (PMMA) and the values for indentation distance increase should fall between 140 and 160 microns. Other calibration materials could be used, including standardized calibration blocks. The values calculated from the calibration indentations are then used to calculate the material strength of the samples taken during the main acquisition (FIG. 11B). Finally, a report is generated (FIG. 11D) and saved to the experiment folder detailing all of the measured parameters.

Figure 12A:
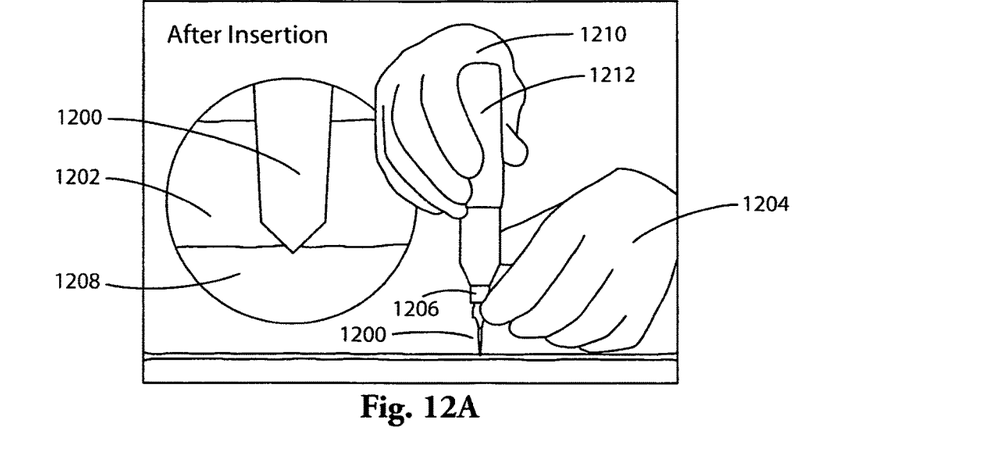
FIGS. 12A, 12B, and 12C illustrate a method of indenting bone through soft tissue with the probe device.
Figure 12B:
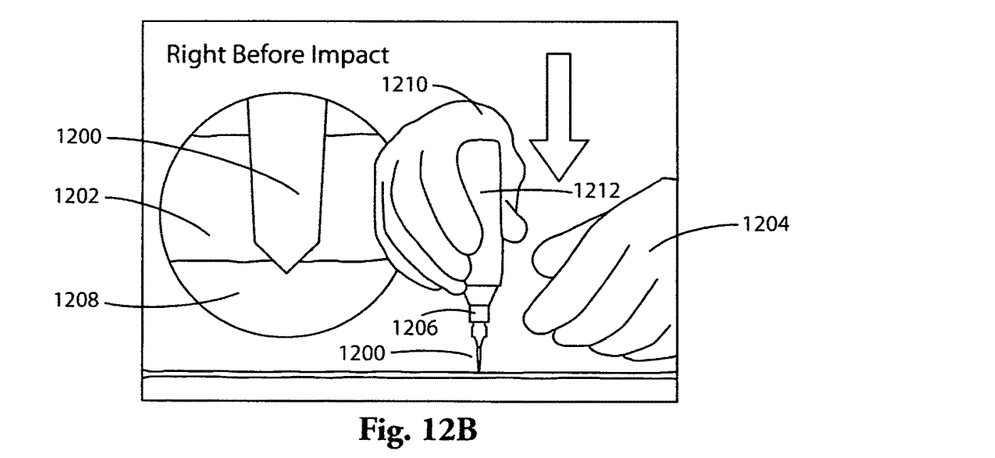
Figure 12C:
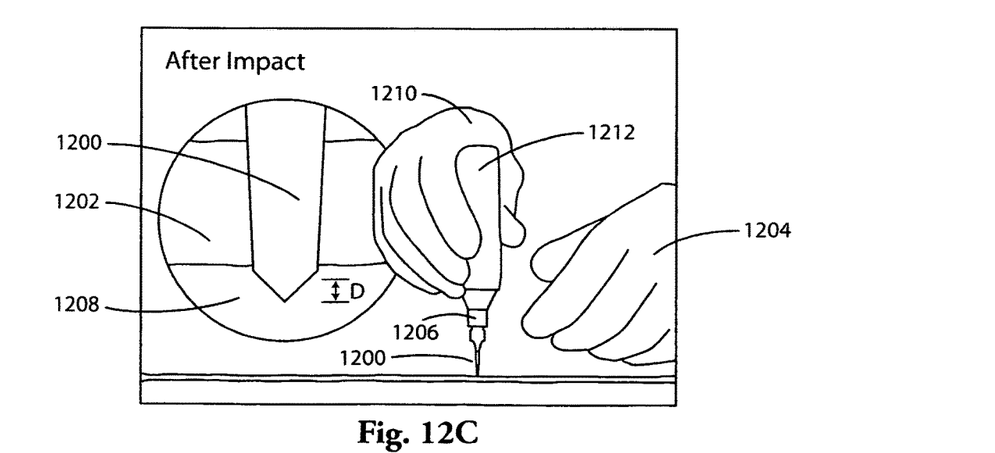

FIG. 12 shows an exemplary technique for testing a sample covered with soft tissue with the instrument. Before the impact (FIG. 12A) the operator will push (or poke) the instrument's probe 1200 through the soft tissue 1202 with their lower hand 1204. The operator's lower hand 1204 will be typically placed on the guide 1206. Once the probe 1200 is advanced through the soft tissue 1202 and resting on the bone 1208 (circular magnified view) the lower hand will generally just be used to stabilize the instrument laterally. The upper hand 1210 on the outer housing 1212 will begin to push downwards in the direction of the arrow (FIG. 12B), compressing the primary spring 218 until the trigger device 228, 928 initiates the impact. This impact will be initiated at a preset force (11N for example). In order that this force remains constant between different impacts, it is important that the lower hand 1204 be neither adding to nor subtracting from this force when the impact is triggered. Thus, in the middle panel (FIG. 12B) the lower hand 1204 is shown having released the instrument before impact. The magnified circular view displays the displacement into the bone 1208 after insertion (FIG. 12B), right before impact (which is the reference point from which the indentation distance increase due to the impact is measured) and after impact (FIG. 12C). This indentation distance increase during the impact (D) illustrated in FIG. 12C is the primary measured parameter from the output signal, and can be subsequently converted to Bone Material Strength as explained herein.

In addition to testing hard samples, such as bone, there are several other applications in soft tissue testing, cosmetics, and quality control. A soft tissue probe (FIG. 3C) that consists of a shaft 330 and a much wider indentation face 332 (~1 cm) can be used to acquire data from soft tissue such as skin, cartilage, and gels. There are cosmetic applications as well, such as testing the fracture resistance of hair with a probe consisting of a shaft and a small flat face (~1 mm). This instrument could be used in quality control applications to test the fracture resistance of materials. The sample being tested does not require any machining or sample preparation so it could be tested in its final production form, making this test very quick and cost effective.

There are several advantages and improvements over existing instruments and techniques. The probe device 100 is much easier to use than prior devices. For the application of measuring bone in living patients prior devices involve scraping away the periosteum, a technique requiring training, for in vivo use with a reference probe. This probe device 100 does not require a reference probe or any scraping, therefore making operator use much easier. The indentation impact is on the order of milliseconds, which is significantly faster than prior devices, making the testing procedure much faster. In one embodiment, the device is mechanically driven, reducing the chance of electrical failures making it safer and more probable for regulatory approval. Finally this instrument is much smaller, allowing for it to be handheld while testing. For the case of measuring materials not covered with soft tissue, such as metals, plastics and composite materials, the advantage over existing devices such as hardness testers is that the device can be hand held and no special sample preparation is required. Thus, for example, the device in the embodiment shown in FIG. 5 can be carried to a rack of materials to select a material with a desired property.

While embodiments of the present invention have been shown and described, various modifications may be made without departing from the scope of the present invention. The invention, therefore, should not be limited, except to the following claims, and their equivalents.

What is claimed is:
1. A probe device for indentation of a material without the use of a reference probe comprising:
   a housing having a mass, wherein the housing comprises an inner housing and an outer housing moveable relative to each other;
   a force generator configured to apply a predetermined force for a predetermined period of time, wherein the force generator is a spring biased impact mass;
   a test probe having a proximal end operatively coupled to the force generator, wherein the probe is designed to penetrate through soft tissue;

a force generator trigger; wherein the trigger comprises a ball trigger disposed in the inner housing and configured to actuate upon contact with the outer housing and, a measurement device configured to monitor the displacement of the test probe upon actuation of the trigger; wherein;

the housing mass, the predetermined force applied by the force generator, and the predetermined time the force is applied are selected such that the housing moves less than 1 µm during displacement of the test probe.

2. The device of claim 1, wherein the measurement device comprises a flexure assembly comprising a plurality of strain gauges.

3. The device of claim 1, further comprising a data acquisition unit having a display configured to output one or more measurements made with the test probe.

4. The device of claim 3, wherein the data acquisition unit is integrated into the housing.

5. The device of claim 3, wherein the data acquisition unit comprises an amplifier operatively coupled to an output of the measurement device.

6. The device of claim 5, further comprising at least one processor configured to receive an output of the amplifier.

7. The device of claim 1, wherein the test probe comprises a probe stop.

8. The device of claim 1, further comprising a level indicator disposed on the housing.

9. The device of claim 1, further comprising a guide member disposed at a distal end of the housing and configured to retain the test probe therein.

10. The device of claim 1, wherein the spring-biased impact mass is interposed in the housing between a primary spring and a secondary spring.

11. The device of claim 1, wherein the device is configured to be hand-held.

12. A probe device for indentation of a material without the use of a reference probe comprising:

a housing having mass;

a force generator configured to apply a predetermined force for a predetermined period of time, wherein the force generator is a spring biased impact mass, and wherein the spring-biased impact mass is interposed in the housing between a primary spring and a secondary spring;

a test probe having a proximal end operatively coupled to the force generator, wherein the probe is designed to penetrate through soft tissue;

a force generator trigger; and, a measurement device configured to monitor the displacement of the test probe upon actuation of the trigger; wherein;

the housing mass, the predetermined force applied by the force generator, and the predetermined time the force is applied are selected such that the housing moves less than 1 µm during displacement of the test probe.

13. The device of claim 12, wherein the measurement device comprises a flexure assembly comprising a plurality of strain gauges.

14. The device of claim 12, further comprising a data acquisition unit having a display configured to output one or more measurements made with the test probe.

15. The device of claim 12, wherein the device is configured to be hand-held.

16. A probe device for indentation of a material without the use of a reference probe comprising:

a housing having a mass, wherein the housing comprises an inner housing and an outer housing moveable relative to each other;

a force generator configured to apply a predetermined force for a predetermined period of time, wherein the force generator is a spring biased impact mass;

a test probe having a proximal end operatively coupled to the force generator, wherein the probe is designed to penetrate through soft substance;

a force generator trigger; wherein the trigger comprises a ball trigger disposed in the inner housing and configured to actuate upon contact with the outer housing and, a measurement device configured to monitor the displacement of the test probe upon actuation of the trigger; wherein;

the housing mass, the predetermined force applied by the force generator, and the predetermined time the force is applied are selected such that the housing moves less than 1 µm during displacement of the test probe.

17. The device of claim 16, wherein the measurement device comprises a flexure assembly comprising a plurality of strain gauges.

18. The device of claim 16, further comprising a data acquisition unit having a display configured to output one or more measurements made with the test probe.

19. The device of claim 16, wherein the device is configured to be hand-held.

* * * * *